United States Patent [19]

Brodman et al.

[11] Patent Number: 4,681,117

[45] Date of Patent: Jul. 21, 1987

[54] INTRACARDIAC CATHETER AND A METHOD FOR DETECTING MYOCARDIAL ISCHEMIA

[76] Inventors: Richard F. Brodman, 3388 Wayne Ave.; Sharon B. Siegel, 3450 Wayne Ave., both of Bronx, N.Y. 10467

[21] Appl. No.: 868,893

[22] Filed: May 27, 1986

Related U.S. Application Data

[63] Continuation-in-part of Ser. No. 466,512, Feb. 15, 1983, abandoned.

[51] Int. Cl.$^4$ .................................................. A61B 5/04
[52] U.S. Cl. .................................................. 128/642
[58] Field of Search .................. 128/642, 784–786, 128/419 P

[56] References Cited

U.S. PATENT DOCUMENTS

| | | | |
|---|---|---|---|
| 1,056,336 | 3/1913 | Hurdman | 128/786 |
| 3,664,347 | 5/1972 | Harmjanz | 128/786 |
| 4,011,861 | 3/1977 | Enger | 128/642 |
| 4,172,451 | 10/1979 | Kline | 128/642 |

FOREIGN PATENT DOCUMENTS 0007157  1/1980  European Pat. Off. ............ 128/784

OTHER PUBLICATIONS

Siegel et al, "Intracardiac Electrode . . . Ischemia", PACE, vol. 5, Nov.–Dec. 1982, pp. 892-902.
Hellerstein et al, "The Electrical Effects of the Injury . . .", Am. H. J., vol. 36, pp. 184-220, 1947.
Mindt, "Stimulating Electrode . . . ", Med. & Biol. Eng., Sep. 1973, pp. 659-660.
Circulation, vol. 66: II-367, Abstract No. 1467, Oct. 1982.
Abstract, "Detection of Ischemia with an Intracavity Electrode," Brodman et al., PACE, vol. 5, Mar.–Apr. 1982, p. 307.

Primary Examiner—Lee S. Cohen
Attorney, Agent, or Firm—Pennie & Edmonds

[57] ABSTRACT

An intracardiac catheter especially well suited to detect electric currents emanating from any part of the heart wall, and a method for, detecting myocardial ischemia. The intracardiac catheter comprises an electric lead that, in turn, includes at least one electric conductor having first and second ends, an electrically insulating sheath covering a substantial portion of the conductor, a sensor connected to the first end of the conductor to detect electric currents inside and emanating from the heart of a subject, and at least one plug connected to the second end of the conductor to connect the electric lead to a monitor. The catheter further comprises a device secured to the electric lead for preventing the sensor from coming into direct contact with the endocardium of the subject's heart.

10 Claims, 8 Drawing Figures

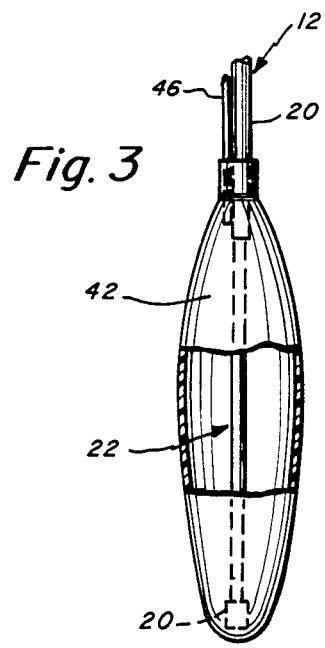
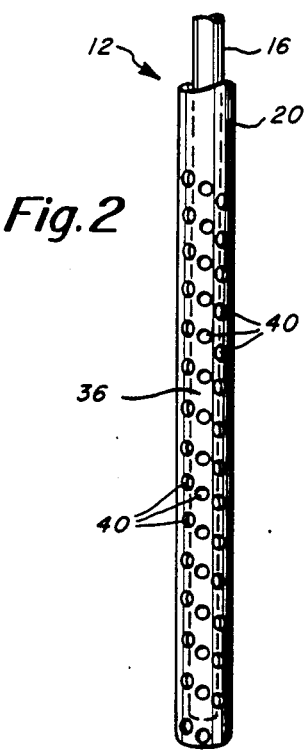
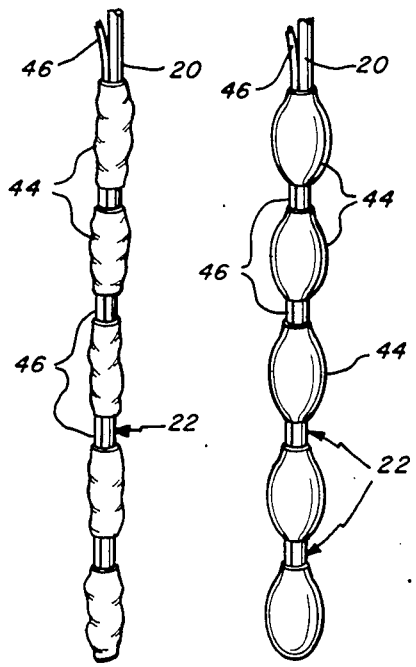
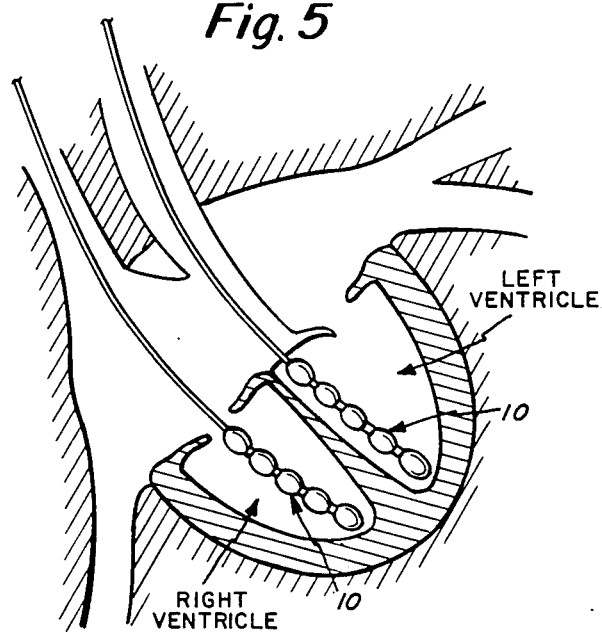

4,681,117

INTRACARDIAC CATHETER AND A METHOD FOR DETECTING MYOCARDIAL ISCHEMIA

BACKGROUND OF THE INVENTION

This is a continuation-in-part of application Ser. No. 466,512, filed Feb. 15, 1983, now abandonded.

This invention generally relates to intracardiac instruments and methods, and more particularly to an intracardiac electrode catheter that is especially well suited for, and to a method for, detecting myocardial ischemia.

Currently available clinical electrocardiographic techniques are deficient in the detection of early or subendocardial ischemia. Also, transmural ischemia may be difficult to assess accurately in the presence of certain disease states or conditions as inflamation of the heart, in peri infarction states, peri-operatively, in the presence of intraventricular conduction defects, and in certain patients with pulmonary disease. Myocardial salvage depends on a reliable means of diagnosing and monitoring ischemia. The invention disclosed herein detects early or subendocardial ischemia as well as transmural ischemia and represents an improvement over currently available techniques for detecting early myocardial ischemia. An electrode designed to detect ischemia wherever it may occur from inside the chambers of the heart is not currently available.

SUMMARY OF THE INVENTION

The present invention is an intracardiac catheter and a method for detecting myocardial ischemia. The electrode catheter is designed so it may be easily passed transvenously into the right ventricular cavity or transarterially into the left ventricular cavity. The electrode catheter is a sensing catheter. It is not designed for cardiac pacing. The electrode catheter senses electrical activity emanating from the heat muscle that is transmitted through the blood in the cardiac chamber to the electrode surfaces, not the local electrogram detected by currently available pacemaker electrodes. The catheter comprises electrode means that may be used as a unipolar, bipolar, or multipolar device based on how the electrode means is connected to a monitor. The sensing electrode surfaces are arranged so as to detect the electric currents from major areas of the heart wall or all of the heart wall. The catheter further comprises means for preventing electrode means from coming into direct contact with the endocardium of the heart of a subject. Since the present invention includes means to prevent the sensing means from contacting the endocardium, even though the electrode means may be located in the close proximity thereto, the present invention does not cause any injury current in the endocardium which would tend to mask the detection of a current of injury caused by a reduction in coronary blood flow. With the present invention, a physician or paraprofessional is able to diagnose subendocardial and transmural ischemia relatively accurately and quickly. This may be done by employing the catheter of the present invention to monitor electric currents emanating from the heart muscle of a subject. The electrode means of the catheter is positioned into the right ventricle from a venipuncture made in an arm vein, the subclavian vein, or femoral vein, or into the left ventrical from the brachial or femoral arteries. Because the electrode means may be inserted into a peripheral vessel, the present invention does not require a surgical procedure. The device, however, may be inserted at open heart surgery.

A BRIEF DESCRIPTION OF THE DRAWINGS

FIG. 2 is a plan view of a portion of an intracardiac catheter in accordance with an alternate embodiment of this invention;

FIG. 3 is a front view, partially in cross section, of a portion of a third embodiment of this invention;

FIG. 4A and 4B are front views illustrating a fourth embodiment of the present invention, wherein a plurality of balloons are used to keep the sensing means of the catheter from contact with the endocardium of the heart of a patient, with the balloons shown collapsed in FIG. 4A and inflated in FIG. 4B;

FIG. 5 is a simplified, cross-sectional view of a heart of a patient, with intracardiac catheters built in accordance with the present invention located in the left and right ventricles of the heart;

Figure 6:
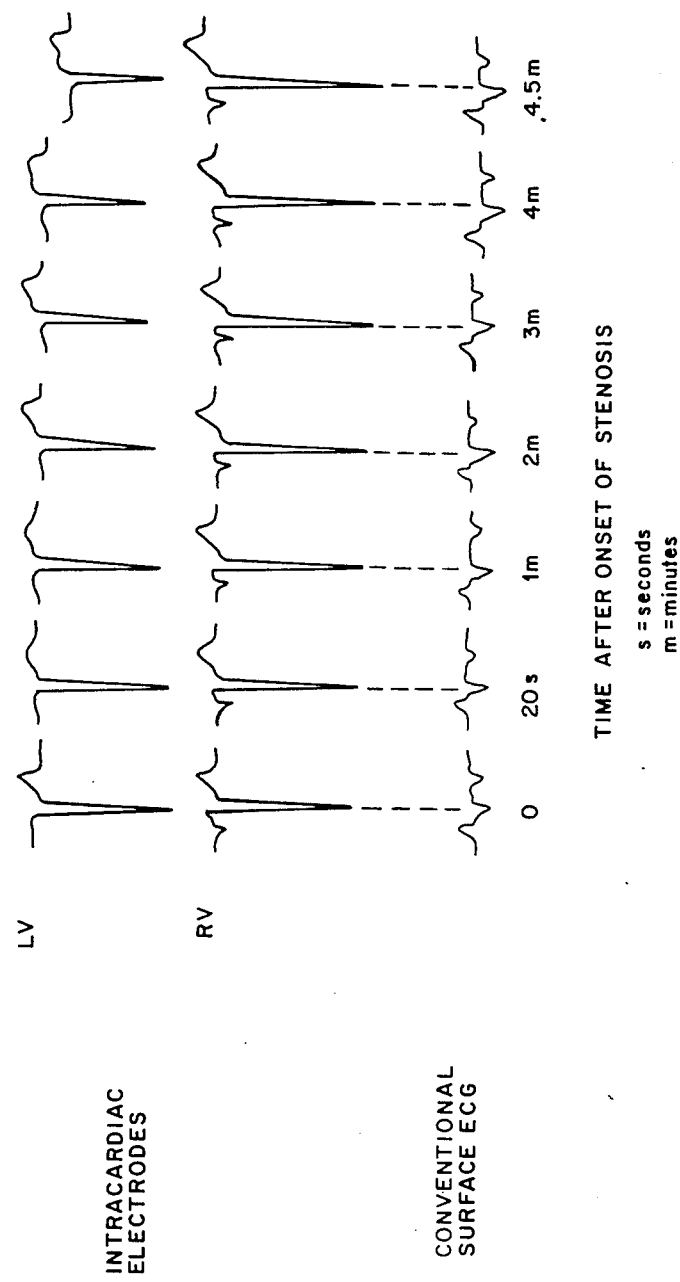
Figure 7:
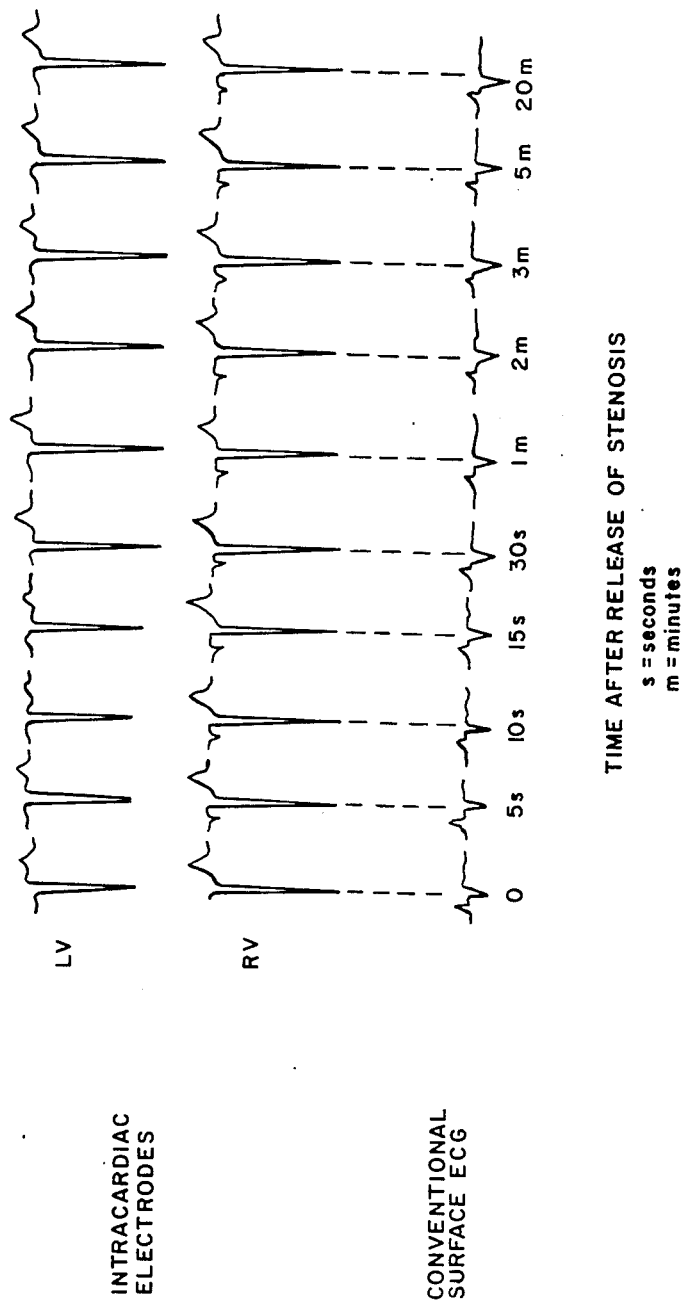

FIG. 6 is an electrocardiogram showing the electric currents detected by the intracardiac catheters shown in FIG. 5 and a surface ECG (Lead II) in a canine experiment where ischemia was induced by a coronary artery stenosis; and FIG. 7 is an electrocardiogram showing the electric currents detected by the intracardiac catheters shown in FIG. 5 and by a conventional surface ECG (Lead II) during release of the coronary artery stenosis.

A DETAILED DESCRIPTION OF THE PREFERRED EMBODIMENT

Figure 1:
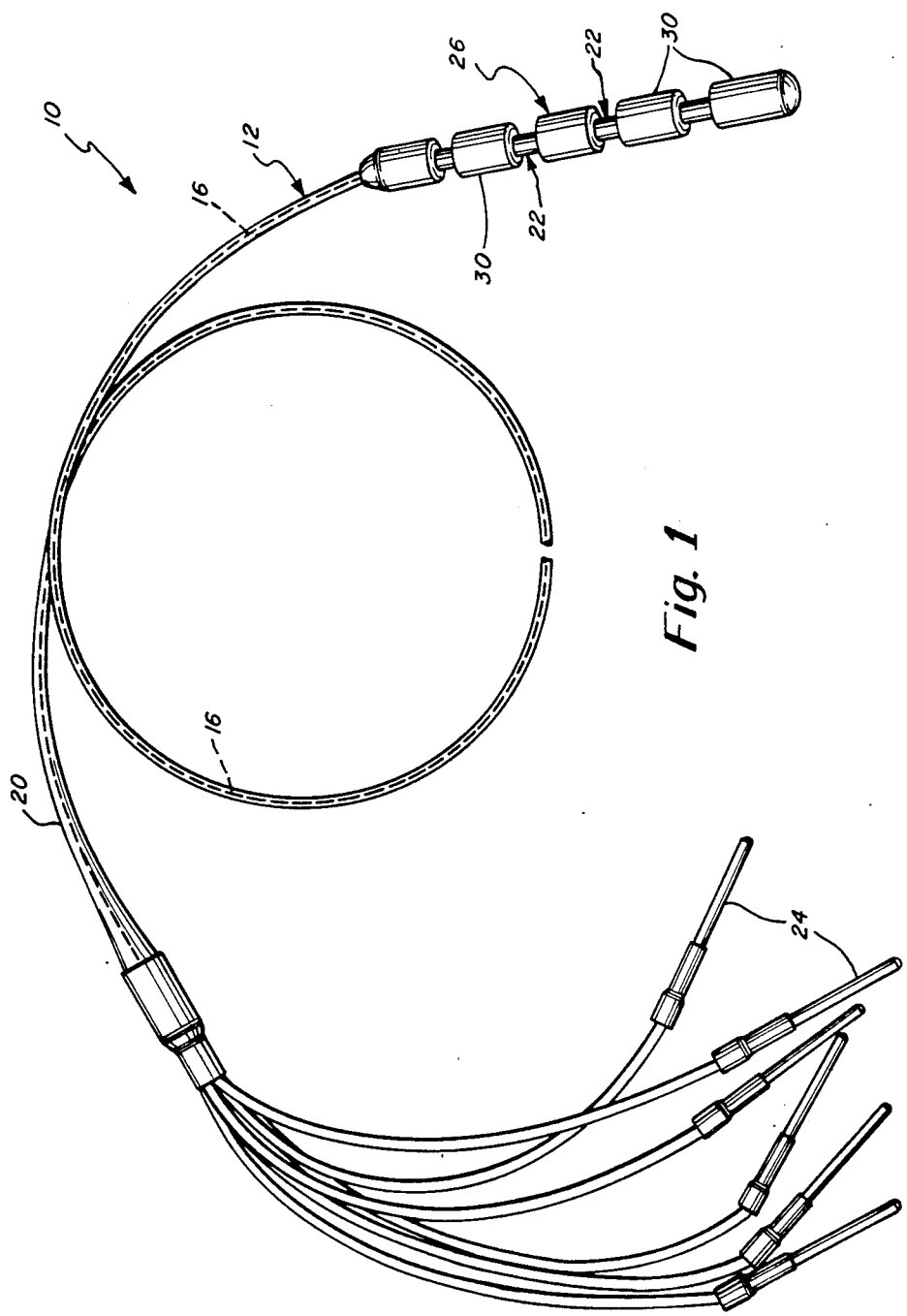
FIG. 1 is a perspective view of portions of a intracardiac catheter in accordance with one embodiment of the present invention.

An intracardiac catheter 10 in accordance with the present invention is shown in FIG. 1. Catheter 10 comprises electric lead 12 which, in turn, includes at least one electric conductor 16, electrically insulating sheath 20, sensing means 22, and at least one plug 24. Conductor 16 has first and second ends and is provided to conduct electric currents therebetween. Sheath 20 covers a substantial portion of conductor 16 to insulate and protect that portion of the conductor. Sensing means 22 is connected to the first end of conductor 16 for detecting, in a manner more fully explained below, electric currents inside of and emanating from the heart of a subject. Plug 24 is connected to the second end of conductor 16 and is provided to connect electric lead 12 to a monitor such as a conventional electrocardiograph display machine that provides an indication, for instance a graphic display, of the currents detected by sensing means 22 as a function of time.

As will be apparent to those skilled in the art, conductor 16, sheath 20, sensing means 22, and plug 24 may all be formed from conventional materials. For example, sensing means 22 may comprise one or more conventional electrodes. Further, preferably electric lead 12 is bipolar, with sensing means 22 including positive and negative electrodes. Of course, other types of electric leads 12, for instance unipolar, hexapolar, or octapolar, may also be employed in the practice of the present invention, and lead 12 may include a plurality of conductors 16 and a plurality of plugs 24.

Catheter 10 further includes means 26 secured to electric lead 12 for preventing sensing means 22 from coming into direct contact with the endocardium of the heart of the subject. In the embodiment of intracardiac catheter 10 illustrated in FIG. 1, means 26 comprises a plurality of bands 30 secured to and radially extending outward from sensing means 22. Bands 30 in turn may be comprised of any suitable insulating material wrapped onto and around portions of sensing means 22.

As will be appreciated, other arrangements may be employed to prevent sensing means 22 from coming into direct contact with the endocardium of the heart. For example, as shown in FIG. 2, insulating material 36, defining a multitude of openings 40, encircles sensing means 22. Insulating material 36 may be integral with sheath 20, or may be connected thereto in any acceptable manner, and material 36 may be applied or attached to sensing means 22. Also, as shown in FIG. 3, an inflatable electrically conductive balloon means 42 may be secured to lead 12 and envelope or enclose sensing means 22. This alternative device is fashioned so sensing means 22 is insulated from direct contact with balloon 42 by insulating sheath 20 at the tip. In FIGS. 4A and 4B, a plurality of inflatable balloons 44, which are not electrically conductive, may be secured to sensing means 22 to keep the sensing means from coming into direct contact with the endocardium of the subject's heart.

With the arrangements shown in FIGS. 3 and 4A and 4B, electric lead 12 further includes tube 46 in communication with the interior of balloon 42 or balloons 44 to conduct a physiologic electrolyte solution such as saline or blood from a reservoir or source located outside a patient into the balloon 42 or balloons 44 to inflate the balloons when sensing means 22 is within a cardiac chamber, and to conduct the solution therefrom to collapse the balloons prior to removal of the sensing means. With a conductive solution in the embodiment of FIG. 3, the sensing means 22 detects electric currents emanating from the blood surrounding conductive balloon 42 via the conductive solution in communication with the interior of the balloon. In all the embodiments of catheter 10 described above, sensing means 22 is covered by means 26, insuring that this electrode tip does not engage the endocardium of the heart as catheter 10 is inserted thereinto.

In all the embodiments illustrated, it will be noted that the tip of the sensing means adjacent the distal tip of the intracardiac electrode that may touch the myocardial surface is insulated so that it is not exposed to the area where the electrode touches the myocardium. Therefore, the sensing means will not detect a current of injury caused by contact of the heart muscle by the electrode.

In operation, sensing means 22 is guided into the interior of the heart of a live subject via a peripheral vessel. While sensing means 22 is inside the heart, means 26, 36, 42, and 46 of the embodiments of FIGS. 1 to 5 respectively, prevent the sensing means from coming into direct contact with the endocardium of the heart. At the same time, however, sensing means 22 is in close proximity to the endocardium of the heart, and blood within the heart conducts electric currents emanating from the heart to the sensing means. These currents are conducted through conductor 16 and, thence, may be observed or monitored in any conventional manner using conventional electrocardiograph equipment. FIG. 5 is a simplified diagram of an example of intracardiac catheters built in accordance with the present invention. The catheters are located in the left and right ventricles of the heart. The electrodes shown are arranged from the apex to the A-V valve annulus of each heart chamber and are capable of detecting electric currents inside and emanating from major areas of the heart wall or all of the heart wall.

Intracardiac catheters 10 as described above were experimentally employed with twenty-two greyhounds, and it is believed that a detailed discussion of these experiments will clearly illustrate the present invention, as well as the advantages and benefits thereof.

The twenty-two greyhounds used were previously trained as running dogs and often had a baseline electrocardiogram which exhibited left ventricular hypertrophy with strain patterns. The dogs, weighing 24–40 kg, were anesthetized wth sodium pentobarbital and ventilated with room air by a conventional volume respirator through a cuffed endotracheal tube. Each dog was given 1.5 cc of a 1 mg/cc solution of Pancuronium initially and approximately 1cc of the solution per hour thereafter to decrease electrical noise caused by skeletal muscle activity. Lidocaine was administered to decrease the incidence of ventricular fibrillation. Two boluses, 1 mg/kg, were given 15 minutes apart and a constant infusion of 70 micrograms/kg/min was maintained thereafter. Procainamide (5 mg/kg over 10 minutes for up to 3 doses) was used in a few experiments when ventricular arrhythmias could not be controlled with lidocaine. Central venous pressure readings from the inferior vena cava were periodically taken and arterial pressure continuously monitored on conventional monitoring equipment such as a DR8 EFM Simultrace Recorder via a standard pressure transducer, for example a Statham pressure transducer.

A left thoracotomy was performed in the fifth intercostal space and the heart of the subject was suspended in a pericardial cradle. The left anterior descending (LAD) artery was dissected free just after its first diagonal and the left circumflex (Cx) artery was isolated just distal to the left artrial appendage. An O-silk suture was looped around each vessel and threaded through a plastic sleeve.

Referring to FIG. 5, a first intracardiac catheter 10 (referred to as the RV catheter) was passed through the left external jugular vein and into the right ventricle of the heart, and a second intracardiac catheter 10 (referred to as the LV catheter) was passed into the left ventricle either through the left carotid artery or the left artrial appendage. Attempts were made to pass the catheters 10 to the apex of the ventricular cavities. Placement of catheters 10 was guided by a standard electrogram and verified by opening the heart in situ at the end of the procedure. In addition to the catheters shown in FIG. 5, a plurality of surface electrodes or leads were attached to the greyhounds in a conventional manner to obtain a standard electrodcardiogram. A conventional electrocardiograph monitor such as Hewlett Packard Model #M06991 was used to observe and record the outputs from these conventionally attached leads as well as the outputs from the RV and LV catheters.

Ninety-eight partial coronary artery occlusions were performed on the twenty-two dogs. In particular, the left anterior descending coronary or the circumflex arteries were stenosed using 1 to 2.5 mm diameter Garrett dilators. Decreasing the dilator size produced progressive diminution of vessel lumen. The silk suture was tightened snugly around the vessel and a dilator by moving the plastic tubing, through which the silk suture was threaded, and securing the tubing with a hemostat. The dilator was immediately removed and the stenosis was maintained for up to twenty minutes. The stenosis was released if significant ischemic changes or arrhythmias occurred. It was intended in this fahsion to produce subendocardial as well as varying degrees of transmural ischemia by progressive occlusions. At the end of the procedure, the internal diameter of the coronary artery at the site of the stenosis was measured using the Garrett dilator and the approximate degree of the coronary artery stenosis was calculated.

During these stenosis, recordings were taken on both the DR8 EFM and the electrocardiograph monitor at 20 sec, 40 sec, 1, 2, 3, 5, 10, 15 and 20 minutes after the onset of the stenosis and more frequently if changes were rapid. A progression of electrograms during one experiment from the onset of a 50% circumflex coronary artery stenosis to four and a half minutes thereafter is shown in FIG. 6. Recordings were also taken at the same time intervals described above or more frequently after release of the stenosis, and a progression of electrograms during one experiment from the time of the release of the 50% circumflex coronary artery stenosis to twenty minutes thereafter is shown in FIG. 7. In most instances, electrograms returned to baseline 20 minutes after release of the stenosis. Each dog underwent one to eight coronary artery stenoses before dying of ventricular fibrillation or cardiogenic shock.

During coronary artery stenoses sufficient to result in any change in the conventional electrocardiograms, there were recognizable changes in 100% of the LV electrograms and 71% of the RV electrograms. Also, of those stenoses which resulted in no change in the conventional electrocardiograms, there were changes in 29% of the LV electrograms (9/31) and 9% of the RV electrograms (3/31).

More specifically, the left ventricular electrograms showed consistent patterns of change in response to significant coronary artery stenosis. Referring to FIG. 6, within twenty seconds of the onset of ischemia, changes appeared and included a decrease in the QS amplitude (less negative), an increase in ST segment elevation, and a decrease in the T wave amplitude. While the QS and ST segment changes progressed with time during the stenosis, the T wave change reversed direction at about 20 seconds to one minute after the start of the stenosis. Referring to FIG. 7, within five seconds after release of the stenosis, the changes to the QS and ST segments and the T wave began to reverse. In particular, the QS amplitude increased (became more negative), the ST segment elevation diminished, and the T wave amplitude decreased. These trends continued, although there was a secondary T wave elevation a few minutes after release of the stenosis, after which the T wave returned to the baseline.

The changes in the RV electrograms were somewhat less consistent, of smaller magnitude, and tended to be the reciprocal of the changes in the LV electrograms. Specifically, the QS complexes generally increased in amplitude (became more negative), the ST segments usually decreased, and the T wave amplitude increased. These changes in the RV electrograms showed rapid reversal upon release of the stenosis.

Evidence of ischemia first appeared on the intracardiac electrograms within about twenty seconds after the onset of the stenosis, but did not appear on the standard electrocardiogram until significantly later. Moreover, upon release of the stenosis, evidence of the reversal of ischemic changes was seen much earlier and more clearly on the intracardiac electrograms than on the conventional electrocardiogram.

Intracardiac electrodes also allowed for the detection of ischemia in the presence of intraventricular conduction defects, strain patterns, and in the peri infarction period.

While the operations described directly above were employed upon animals, the present invention, with modifications well within the purview of those of ordinary skill in the art, may also be employed on people. Preferably, though, if this procedure is applied to a human patient, the left ventricle electrode is inserted through a peripheral artery such as the femoral or brachial arteries and moved downstream through the aortic valve into the left ventricle; and the right ventricle electrode is inserted trough a peripheral vein such as a brachial, femoral, or subclavian vein and moved upstream into the right ventricle of the heart.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

We claim:

1. An intracardiac catheter for transmitting electric currents from the heart of a living subject to a monitor comprising: and electric lead including at least one electric conductor having first and second ends, an electrically insulating sheath covering a substantial portion of the conductor, sensing means connected to the first end of the conductor capable of detecting electric currents inside and emanating from major areas of the heart wall or all of the heart wall, and means connected to the second end of the conductor to connect the electric lead to the monitor; and means secured to the electric lead for preventing the sensing means from coming into direct contact with the endocardium of the heart for preventing the sensing means from causing a current of injury, said electric lead, sensing means and means preventing the sensing means from coming into contact with the endocardium being sized to pass transvenously or transarterially into a ventricle of the heart.

2. An intracardiac catheter according to claim 1 wherein the means for preventing the sensing means from coming into direct contact with the endocardium includes band means secured to and radially extending outward from the sensing means.

3. An intracardiac catheter according to claim 1 wherein the means for preventing the sensing means from coming into contact with the endocardium includes an insulating material defining a plurality of openings and extending around the sensing means.

4. An intracardiac catheter according to claim 3 wherein the insulating material extending around the sensing means is integral with the sheath.

5. An intracardiac catheter according to claim 1 wherein the sensing means has a distal tip remote from the second end of the electric lead, and the means for preventing the sensing means from coming into direct contact with the endocardium includes electrical insulation covering the distal tip of the sensing means.

6. An intracardiac catheter according to claim 1 wherein the means for preventing the sensing means includes electrically conductive balloon means for enclosing the sensing means.

7. An intracardiac catheter according to claim 6, wherein the electric lead further comprises tube means in communication with the interior of said balloon means for directing an electrically conductive solution into and out of said balloon means.

8. A method for detecting myocardial ischemia in a living subject comprising:
   inserting sensing means into the interior of the heart of the subject through a vein or artery;
   preventing the sensing means from coming into direct contact with the endocardium of the heart for preventing the sensing means from producing a current of injury and arranged so as not to reduce the signal strength of the electric currents emanating from the heart; and
   detecting electric currents inside and emanating from major areas of the heart wall or all of the heart wall through the sensing means.

9. The method of claim 8 which further comprises preventing said sensing means from coming into direct contact with the endocardium by enclosing said sensing means within inflatable balloon means; said balloon means being fabricated from an electrically conductive material.

10. The method of claim 9 which further comprises inflating said balloon means for preventing the sensing means from coming into direct contact with the endocardium by directing an electrically conductive solution from reservoir or source means outside of the subject into the interior of the balloon means.

* * * * *

UNITED STATES PATENT AND TRADEMARK OFFICE
CERTIFICATE OF CORRECTION

PATENT NO.  : 4,681,117
DATED       : July 21, 1987
INVENTOR(S) : Richard F. Brodman et al It is certified that error appears in the above-identified patent and that said Letters Patent is hereby corrected as shown below:

On the title page, "Inventors" should read:

-- [76] Inventor:  Richard F. Brodman
                   3388 Wayne Ave.
                   Bronx, NY  10467 --.

Signed and Sealed this

Fifteenth Day of December, 1987

Attest:

DONALD J. QUIGG

Attesting Officer           Commissioner of Patents and Trademarks